US008301260B2

(12) United States Patent
Daglow

(10) Patent No.: US 8,301,260 B2
(45) Date of Patent: Oct. 30, 2012

(54) METHOD OF IMPLANTING A MEDICAL IMPLANT TO TREAT HEARING LOSS IN A PATIENT, DEVICES FOR FACILITING IMPLANTATION OF SUCH DEVICES, AND MEDICAL IMPLANTS FOR TREATING HEARING LOSS

(76) Inventor: Terry D. Daglow, Bonham, TX (US)

( * ) Notice: Subject to any disclaimer, the term of this patent is extended or adjusted under 35 U.S.C. 154(b) by 420 days.

(21) Appl. No.: 12/539,027

(22) Filed: Aug. 11, 2009

(65) Prior Publication Data
US 2010/0042184 A1    Feb. 18, 2010

Related U.S. Application Data

(60) Provisional application No. 61/088,692, filed on Aug. 13, 2008.

(51) Int. Cl.
*A61N 1/05* (2006.01)
(52) U.S. Cl. .......................................................... 607/57
(58) Field of Classification Search .............. 607/55–57, 607/137; 606/109; 623/10, 24–25
See application file for complete search history.

(56) References Cited

U.S. PATENT DOCUMENTS

| 4,988,333 A | 1/1991 | Engebretson et al. |
| 5,176,620 A | 1/1993 | Gilman |
| 5,531,787 A | 7/1996 | Lesinski et al. |
| 5,772,575 A | 6/1998 | Lesinski et al. |
| 5,881,158 A | 3/1999 | Lesinski et al. |
| 5,951,601 A | 9/1999 | Lesinski et al. |
| 5,977,689 A | 11/1999 | Neukermans |
| 5,984,859 A | 11/1999 | Lesinski |
| 6,068,589 A | 5/2000 | Neukermans |
| 6,153,966 A | 11/2000 | Neukermans |
| 6,190,305 B1 | 2/2001 | Ball et al. |
| 6,224,604 B1 | 5/2001 | Suddaby |
| 6,381,336 B1 | 4/2002 | Lesinski |
| 6,561,231 B2 | 5/2003 | Neukermans |
| 2006/0184143 A1* | 8/2006 | Jolly et al. ............... 604/288.02 |
| 2007/0225776 A1* | 9/2007 | Fritsch et al. .................... 607/57 |
| 2007/0228071 A1* | 10/2007 | Kamen et al. .................... 222/52 |
| 2008/0064918 A1* | 3/2008 | Jolly .............................. 600/25 |
| 2008/0154250 A1 | 6/2008 | Makower et al. |

FOREIGN PATENT DOCUMENTS

| DE | 3940632 C1 | 12/1990 |
| DE | 4221866 A1 | 1/1994 |
| GB | 2181622 A | 4/1987 |
| WO | 2008/077943 A2 | 7/2008 |

* cited by examiner

*Primary Examiner* — Niketa Patel
*Assistant Examiner* — Hiba El-Kaissi
(74) *Attorney, Agent, or Firm* — George M. Tompkins

(57) ABSTRACT

In one embodiment, a method of treating hearing loss in a patient, comprises: creating a first channel in osseous tissue at or immediately adjacent to the promontory of the patient; creating a second channel through the first channel to the scala tympani or the scala vestibuli; and implanting a hearing device in the first channel, the hearing device being in fluid communication with cochlear fluid through the second channel, the hearing device being adapted to drive cochlear fluid to activate auditory receptor cells in the cochlea of the patient.

8 Claims, 17 Drawing Sheets

METHOD OF IMPLANTING A MEDICAL IMPLANT TO TREAT HEARING LOSS IN A PATIENT, DEVICES FOR FACILITING IMPLANTATION OF SUCH DEVICES, AND MEDICAL IMPLANTS FOR TREATING HEARING LOSS

RELATED APPLICATION

This application claims the benefit of U.S. Provisional Patent Application Ser. No. 61/088,692, filed Aug. 13, 2008, which is incorporated herein by reference.

BACKGROUND

In normal human hearing, acoustical energy in the form of sound waves is directed into the ear canal of a human by an outer ear. The sound waves impinge upon a tympanic membrane, i.e. the eardrum, located at the inner end of an outer ear canal. The pressure of the sound waves causes tympanic vibrations in the eardrum, thereby producing mechanical energy.

Three interconnected bones, referred to as the ossicular chain, transfer these tympanic vibrations of the eardrum across a middle ear cavity and into an inner ear. The ossicular chain includes three major bones, the malleus, the incus and the stapes. The stapes resides in the oval window, attached to its margins by the annular ligament. The oval window serves as the entrance to the inner ear.

Mechanical vibrations conducted to the oval window generate vibrations within the inner ear fluids, the perilymph and then the endolymph. The hearing portion of the inner ear is a hollow, spiral otic capsule bone shaped like a snail shell and called the cochlea. The cochlea is divided into three chambers, the scala vestibuli, scala tympani which contain perilymph, and the scala media which contains endolymph. Sound vibrations (pressure waves) enter the perilymph of scala vestibuli and are transmitted to scala media across a thin elastic membrane (Reisner's membrane). The floor of scala media is the basilar membrane, a flexible membrane which has an elasticity gradient progressing from stiff to flexible. The varying resonant characteristics of the basilar membrane permit pitch differentiation with the basal coil of the cochlea being sensitive to high frequencies and the apical to low frequencies. Positioned on the basilar membrane are 16,000 receptor cells ("hair cells") arranged in three rows of outer hair cells, and one row of inner hair cells. The cilia of these hair cells insert into a rigid tectorial membrane. As the basilar membrane is displaced upward the cilia bend, the shearing effect produces a change in membrane permeability of the hair cells and potassium contained in the potassium rich endolymph invades the hair cells, depolarizing the cell. The bases of the hair cells are innervated by auditory nerve fibers which are activated by this depolarization. The auditory nerve fibers then transmit signals ultimately to the temporal lobe of the brain where the subject consciously perceives sound.

Generally, hearing difficulties fall into one of two categories. Conductive hearing loss relates to the inability, or inefficiency, in mechanically conveying the vibrations caused by sound waves through the outer ear, the middle ear and the oval window to the perilymph. Sensorineural hearing impairment relates to deterioration of the receptor cells or nerve fibers within the inner ear, so that fluid vibrations within the inner ear are not properly converted to nerve impulses and thus inadequately transmitted to the brain.

Hearing loss is typically treated using two different types of hearing devices. The most common category of device is the hearing aid. For more significant hearing impairments, cochlear implants are employed.

Hearing aids simply provide a form (via analog or digital processing) of acoustical gain to improve the hearing of patients with hearing loss. There are a variety of forms of hearing aids to account for preferences of the various patients and their respective degrees of hearing loss. A number of hearing aids include a "behind-the-ear" component and an "in-the-ear" component. Relatively mild hearing loss can be addressed using "in-the-ear" components that do not completely seal the ear canal. However, to achieve greater acoustical gain for patients with greater hearing loss, other known in-the-ear components seal the ear canal. Some patients can find devices that seal the ear canal to be uncomfortable or undesirable in some respects. Due to a number of issues, many patients suffering from hearing loss choose not to use their hearing aids for a significant amount of time or at all.

Instead of merely amplifying acoustical signals, cochlear implants process acoustical signals and generate electrical currents for stimulation of neural tissue of the cochlea. Typically, a cochlear system will include a behind-the-ear component that samples acoustical signals and processes the sampled signals using a digital signal processor and various processing algorithms. Cochlear systems also include multi-current sources for generating stimulation currents corresponding to various frequency bands of the processed signals. The multi-stimulation currents are applied to different portions of the cochlea by respective electrodes of a cochlear lead. Also, it is noted that implantation of the cochlear lead is a relatively delicate process. Due to these considerations, cochlear implants are only utilized for patients with relatively profound hearing losses.

SUMMARY

Some representative embodiments provide unique methods of implanting a medical device within a patient to address the hearing loss of a patient. In some embodiments, one or more channels are drilled through the promontory of the patient to access one or more of the scala vestibuli, scala tympani, and the scala media. A number of embodiments provide different types of implantable devices that can be fluidically or otherwise coupled therewith. A passive diaphragm-type device may be coupled therethrough to transfer acoustical signals to the cochlear fluid. A magnetically driven or piezo driven diaphragm can also be utilized to drive the cochlear fluid. In one alternative embodiment, a fluidic drive device can be utilized to drive the cochlear fluid.

By utilizing the promontory as a location to gain access to cochlear regions, some embodiments provide a number of advantages. For example, the promontory provides a unique access point in which any of the scala vestibuli, the scala tympani, and the scala media can be reached using certain tools provided by some embodiments and conventional endoscopic equipment. Some embodiments enable the cochlear fluid to be driven in a more physiological compatible manner than certain other known surgical techniques. Furthermore, the selection of the promontory as an access point enables a surgical procedure to access the cochlear fluid to occur in an efficient, safe manner.

In some preferred embodiments, a primary channel formed through the promontory to access cochlear fluid is not uniform in diameter, but rather includes an annular cavity or other indentation within a portion of the channel that extends beyond the diameter of the rest of the channel. The cavity or indentation enables a fluid seal to be achieved by corresponding deformable material of medical implants adapted for use with such channels. Furthermore, the use of deformable material on the implants for coupling within the cavity or indentation of a channel provides a robust stabilizing mechanism for retaining the respective implant within the channel.

In some embodiments, one or more drilling tools are provided that facilitate access to the scala vestibuli, scala tympani, and or scale media. In one embodiment, a drill type device with a first drill bit is utilized to create a first aperture or hole into but not penetrating through osseous tissue at the promontory. A second drill bit according to one embodiment is then utilized by the physician to create the cavity or indentation within the first aperture or hole. The second drill bit comprises a tip that extends generally perpendicularly relative to the axis of the first aperture or hole thereby allowing a gradual increase in the cutting diameter and forming the side cavity or indentation. In one embodiment, the tip is implemented utilizing a Nitinol wire to allow the wire to extend radially away from the axial portion of the drill bit. Another drill bit is utilized and positioned in an angular manner so as to position a tip of the drill bit against a surface of the cavity or indentation and a shaft of the bit is positioned an upper portion the first aperture of hole. By positioning, the drill bit in this manner, an angular channel can then be obtained to access the scala vestibuli or the scale tympani depending upon the relative direction of the tip and the shaft of the drill bit.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Figure 1:
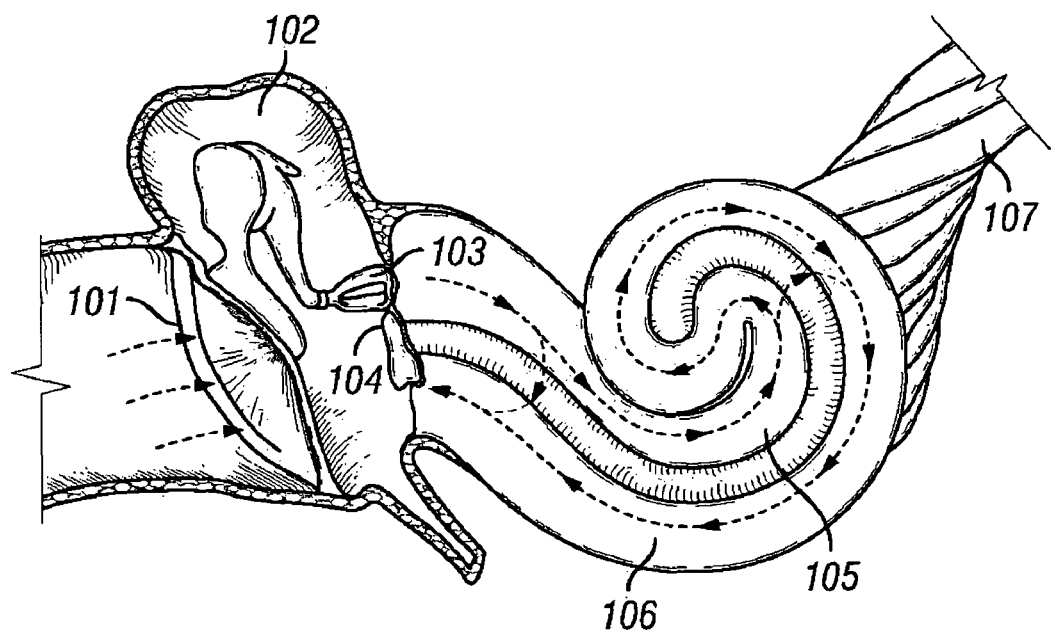
FIG. 1 depicts a simplified illustration of the human ear.
Figure 2:
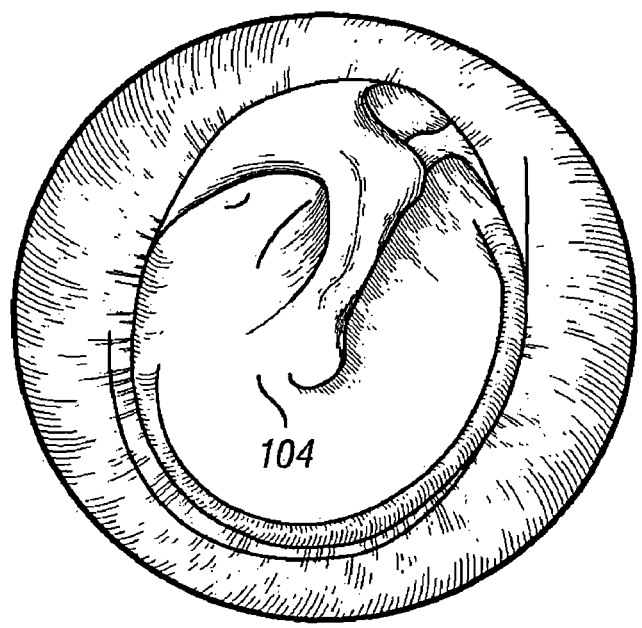
FIG. 2 depicts a view of various osseous structures through the eardrum of a patient.

FIG. 1 depicts a simplified illustration of the human ear. Sound vibrations strike the eardrum 101 which, in turn, contacts the first of the auditory ossicles (i.e., the malleus). The footplate of the last of the ossicles (i.e., the stapes) moves at the oval window 103. Movement at the oval windows causes fluid inside the scala vesibuli 105 and the scala tympani 106 to move. Fluid movement within the cochlear duct causes action potentials in neural tissue which are carried to the brain via the cochlear nerve 107. As shown in FIG. 1, the promontory 104 is a distinct feature in osseous tissue adjacent to the cochlear region. FIG. 2 depicts a view through the eardrum of a patient. As seen in FIG. 2, the promontory 104 is a prominent and typically readily identifiable feature visually disposed below the malleus, incus, and stapes.

Some representative embodiments involve treating hearing loss in a patient by, in part, accessing cochlear fluid in a unique manner. FIGS. 3A-3K depict a method of obtaining fluid access to cochlear fluid for the purpose of treating hearing loss according to one representative embodiment.

Figure 3A:
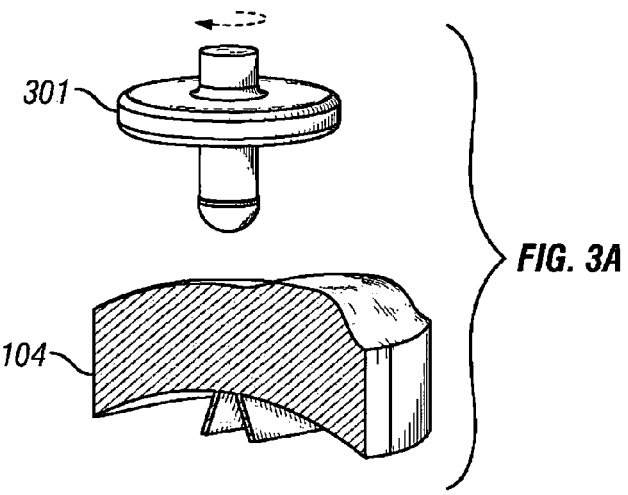
FIGS. 3A-3I depict a method of obtaining fluid access to cochlear fluid for the purpose of treating hearing loss according to one representative embodiment.
Figure 3B:
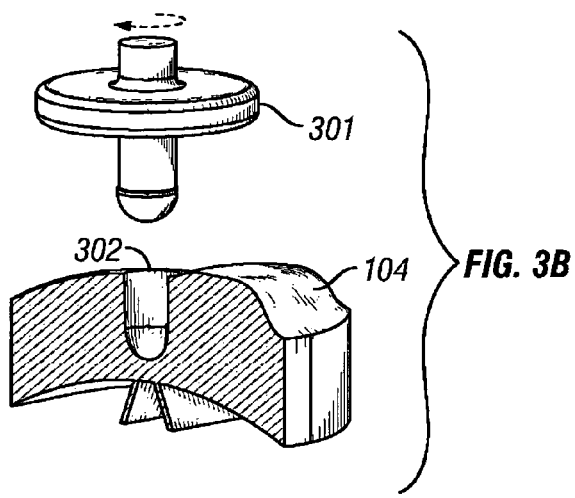
Figure 3C:
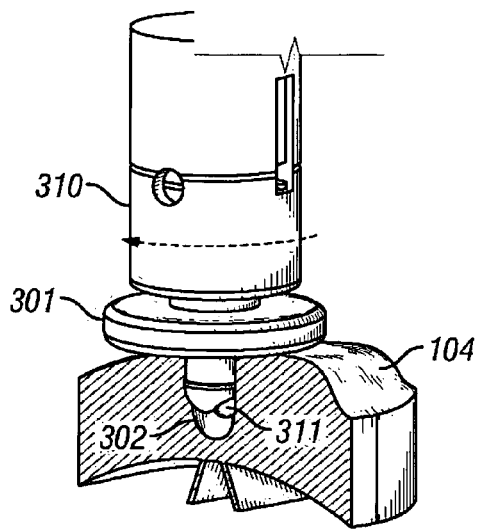
Figure 3D:
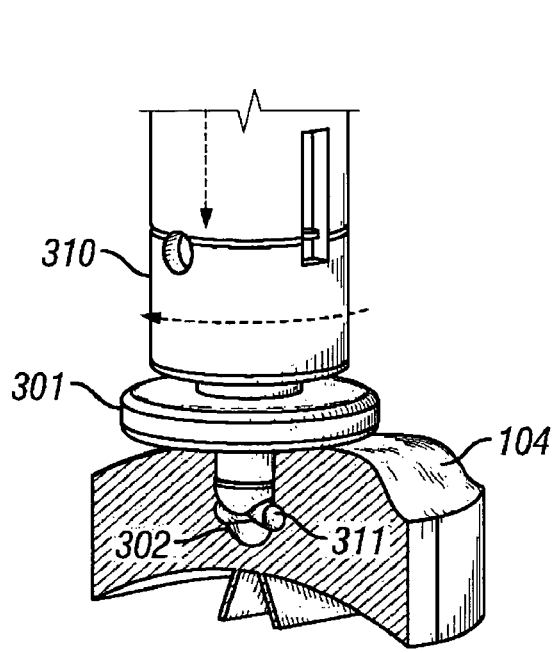
Figure 3E:
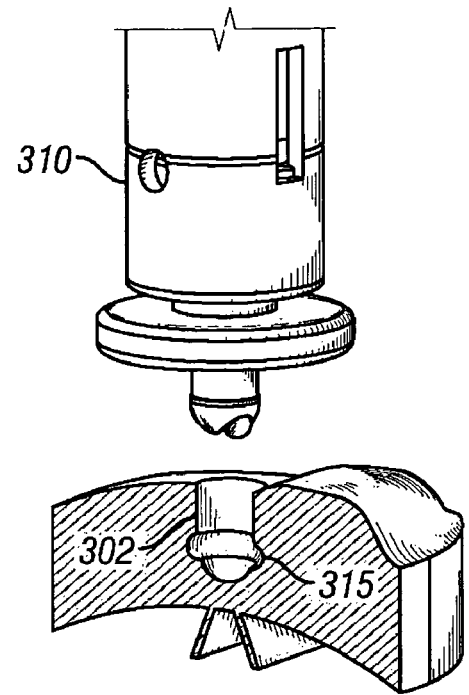
Figure 3F:
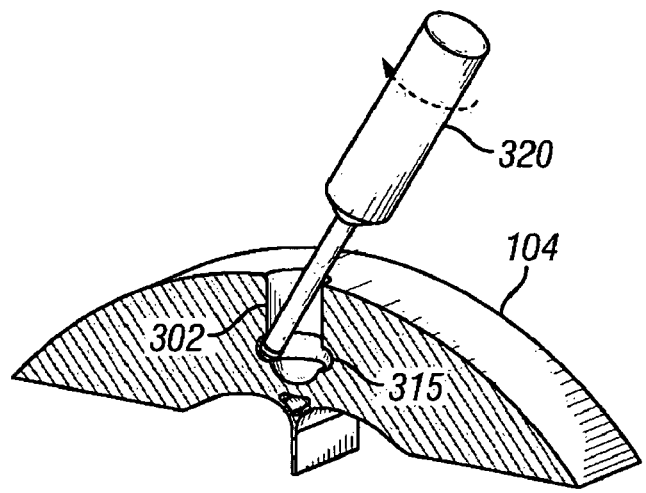
Figure 3G:
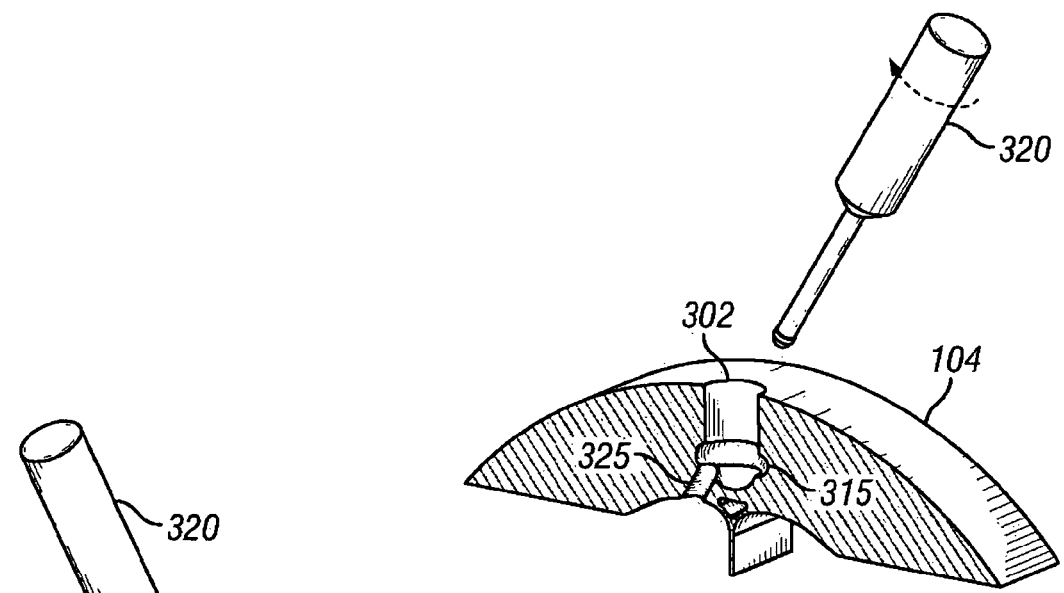
Figure 3H:
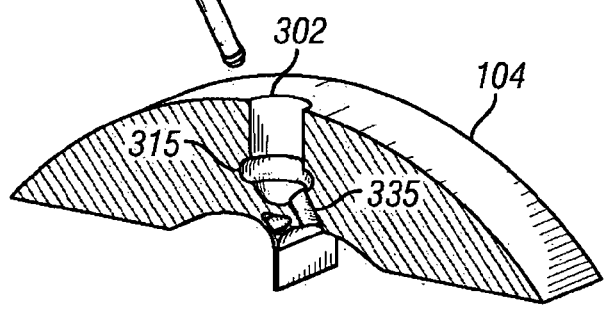
Figure 3I:
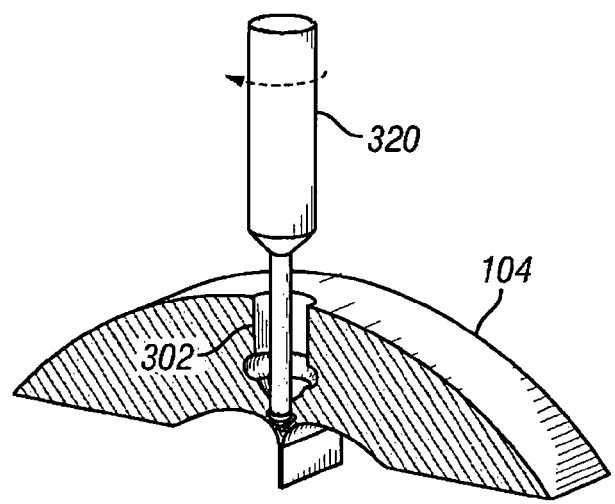
Figure 3J:
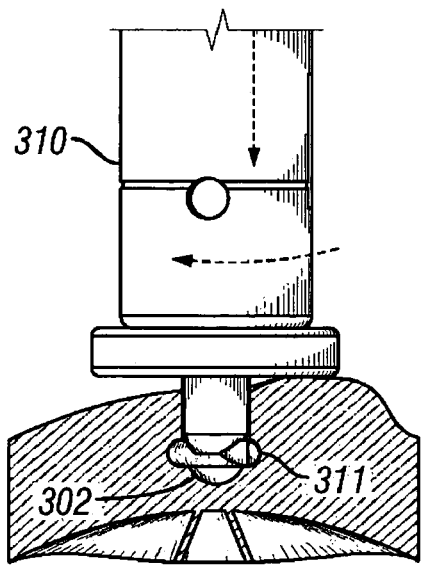
Figure 3K:
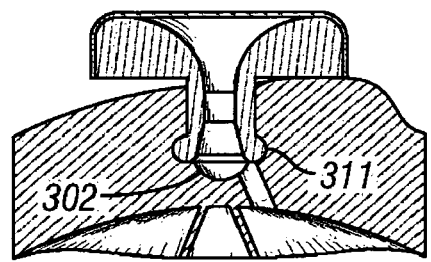

As shown in FIGS. 3A and 3B and 3K, tip 301 of a shouldered custom drill bit is brought in proximity to promontory 104 and a primary hole or channel 302 is created in the promontory 104. Drill bit 310 may be attached to conventional medical drills which are commercially available. The outer most distal surface of the shouldered drill bit will create an imaginary plane tangent to the most distal uneven surface of the promontory and will provide a stopping point that will determine the final depth of the hole or channel. It is this stopping point on an uneven surface where the final hearing device will rest as shown in FIG. 3K, allowing the mating cavities to remain parallel. It is intended that the outer most diameter of the shouldered drill will be equal or larger than the outer most perimeter of the implanted hearing device in the general area of the uneven most distal surface of the promontory. The shouldered custom drill bit may be brought into the suitable position using conventional microscope techniques. This introduction is prior to conducting a tympanoplasty to create an opening through and around the tympanic membrane.

As shown in FIGS. 3C-3E, drill bit 310 of one representative embodiment is then brought into proximity with promontory 104 with cutting portion 311 inserted within hole 302. Drill bit 310 may be attached to conventional medical drills which are commercially available. The operation of the drill causes rotation of drill bit 310. As shown in FIG. 3D, as drill bit 310 is rotated by the drill, the drill bit 310 is placed in the hole or channel 302 as shown in FIG. 3C, the shoulder of the drill bit contacts the outer most uneven surface of the promontory. The cutting portion 311 is extended as additional pressure is applied between the drill bit shoulder and the outer most uneven surface of the promontory, as seen in FIG. 3D, cutting portion 311 removes osseous tissue from the side of hole 302. Side cavity 315 is created within hole 302, the operation of the drill is halted, cutting portion 311 is retracted in the absence of axial or downward pressure, and drill bit 310 is removed from hole 302. Side cavity 315 then provides a feature to hold hearing devices and enables a precise fluid seal to be obtained as seen in FIG. 3K.

After the initial hole 302 and side cavity 315 are formed, another drill bit 320 is employed. In one embodiment, the tip of drill bit 320 is positioned against a wall of side cavity 315 and a portion of the shaft of the drill bit 320 is positioned against an outer portion of hole 302 as shown in FIG. 3F. The trajectory formed by such placement provides an efficient method to permit access to either the scala tympani or the scala vestibuli depending upon the particular direction or angle of the drill bit. Drill bit 320 is then rotated by a conventional medical drill to create channel 325 and/or channel 335 to the scala tympani and/or the scala vestibuli as shown respectively in FIGS. 3G and 3H. Access to the scala media can also be obtained by creating a channel by drilling through the bottom of hole 302 as shown in FIG. 3I.

At this point, an implantable device adapted to treat the patient's hearing loss is implanted in hole 302. The device may also occupy the hole or channels of 325 and 335 and that created into the scala media. In one embodiment, an additional tube may be inserted to reduce or prohibit the holes of 325 and 335 from being reduced in diameter by new osseous growth.

Figure 4A:
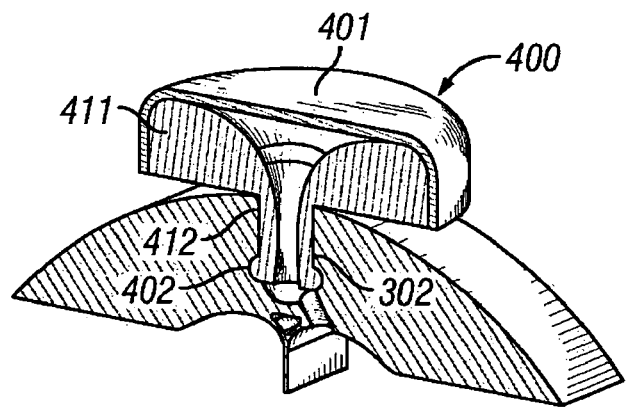
FIG. 4A depicts a diaphragm device for treating hearing loss according to one representative embodiment.

FIG. 4A depicts diaphragm device 400 implanted within hole 302. Device 400 comprises device body 411 and neck portion 412. Neck portion 412 extends into hole 302. Preferably, neck portion 412 comprises deformable section 402 which is adapted to the compressed within cavity 315. The compression of the material of section 402 allows a robust fluid seal to be obtained. Also, the compression of the material of section 402 mechanically holds device 400 in place. Device 412 is preferably adapted to permit cochlear fluid to flow into the interior of device 400. As shown in FIG. 4A, the cochlear fluid is permitted to directly contact the underside portion of diaphragm 401. Device 400 is a passive device in that device 400 transfers or converts acoustical vibrations in the air of the ear canal into movement in the cochlear fluid in one or more of the scala tympani, scala vestibuli, and scala media. That is, vibrations in the ear canal contact diaphragm 401 which, in turn, drives movement in the cochlear fluid. This induced movement of the cochlear fluid is believed to permit partial or complete recovery of hearing for the patient in many cases.

In one preferred embodiment, diaphragm 401 has a diameter of approximately 0.09 inches and has a surface area of approximately 0.0064 inches$_2$. In one preferred embodiment, the channel to the scala tympani or to the scala vestibuli comprises a diameter of approximately 0.015 inches and has a cross-sectional area of approximately 0.0002 inches$_2$. At the entry point into the respective scala, such an arrangement could potentially provide an amplification of approximately 32 to 1. In one embodiment, the base of device 400 could be machined out of polyetheretherketone (PEEK). The diaphragm could be provided by forming one or several layers of material in the aperture defined by the base of device 400. An initial layer of polymer material can be applied to the aperture defined by the base of device 400 by dipping the aperture into polymer material whereby surface tension of the polymer could cause a thin layer to be suspended across the aperture. One or more subsequent polymer layers may be applied thereto after the liquid polymer material cures or is otherwise is transformed into solid form. Also, one or more layers could be metal plated, sputtered, or plasma coated. The polymer layers may be applied in sequence or in alternation with the other material layers. Laser ablation can be applied to one or more of the lasers to define any suitable patterns in the material(s).

In some embodiments, device 400 is tuned to a frequency or frequency range corresponding to hearing loss of the patient. For example, the diaphragm could be molded to include features that control the frequency response of diaphragm 401. Alternatively, features could be laser ablated into diaphragm 401 to modify its frequency response. For example, a spiral pattern could be ablated into diaphragm 401 whereby the "tightness" of the spiral about multiple turns is controlled to modify the frequency response in a manner most beneficial to a particular patient. Also, the particular diaphragm 401 for a patient could be specifically fabricated for the respective patient. For example, a hearing exam may be performed to quantify the hearing loss and a suitable diaphragm 401 could be fabricated to possess a frequency response corresponding to the results of the examination.

Figure 4B:
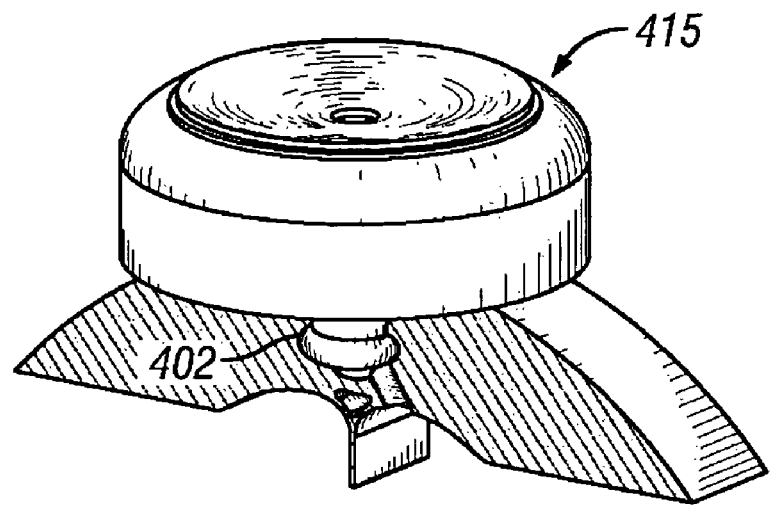
FIG. 4B depicts a diaphragm device for treating hear according to another representative embodiment.

FIG. 4B depicts another diaphragm device 415 for treating hear loss of a patient according to another representative embodiment. Diaphragm device 415 differs from device 400 in that device 415 is adapted to contact the umbo of the patient. For a single chamber device where the outer cover or shell would have a single point contact on the center of the diaphragm, the outer edge would contact the Umba or Mallius and transmit the tympanic membrane motion to the center of the diaphragm. This motion would then be amplified by fluidic displacement.

For a dual chamber device, the outer cover contact point would be located just of center and would need to be oriented in the direction of the Umba or Mallius. The base would have a dividing wall to isolate the chambers and provide a pivot point for creating a negative pressure on the opposite side of the contact point. This process would further amplify the fluidic energy across the Scala Media driven by the movement of the tympanic membrane.

Figure 4C:
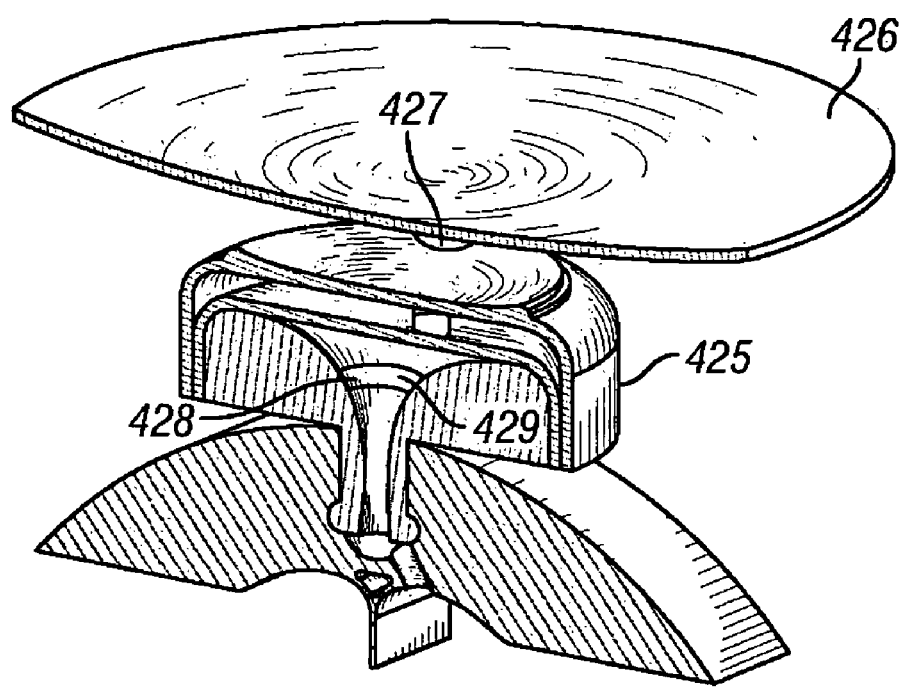
FIG. 4C depicts a diaphragm device for treating hearing loss according to another representative embodiment.

FIG. 4C depicts another diaphragm device 425 for treating hearing loss of a patient according to another representative embodiment. Device 425 is similar to device 415 in that device 425 is adapted to contact the umbo 427 (partially obscured by ear drum 426) of the patient. Device 435 differs from device 425 in that device 435 comprises dual chambers 428 and 429. Chambers 428 and 429 are separately in fluid communication with the scala tympani and the scala vestibuli, respectively. This design permits a positive pressure to be created in one of the scala while simultaneously a negative pressure is created in the other scala.

Figure 4D:
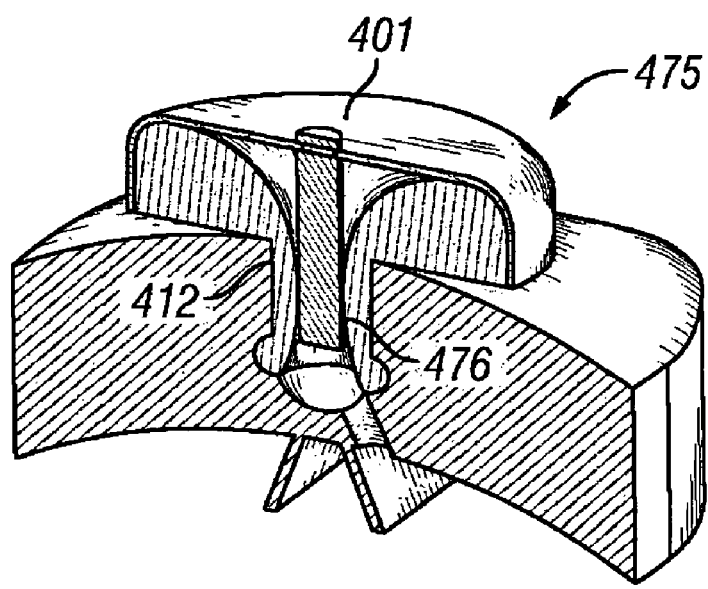
FIG. 4D depict a diaphragm device for treating hearing loss of a patient according to another representative embodiment.

FIG. 4D depict diaphragm device 475 for treating hearing loss of a patient according to another representative embodiment. Diaphragm device 475 differs from device 400 in that device 475 comprises piston 476 attached to diaphragm 401. Piston 476 extends into neck portion 412. As diaphragm vibrates in response to sound waves, piston 476 drives fluid within neck portion 412.

Figure 5A:
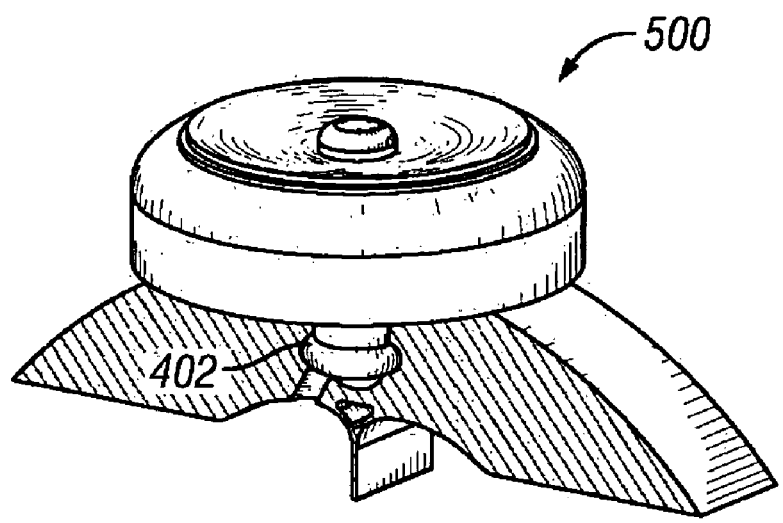
FIG. 5A depicts a diaphragm device in which ferrous magnetic material is attached to the diaphragm according to another representative embodiment.
Figure 5B:
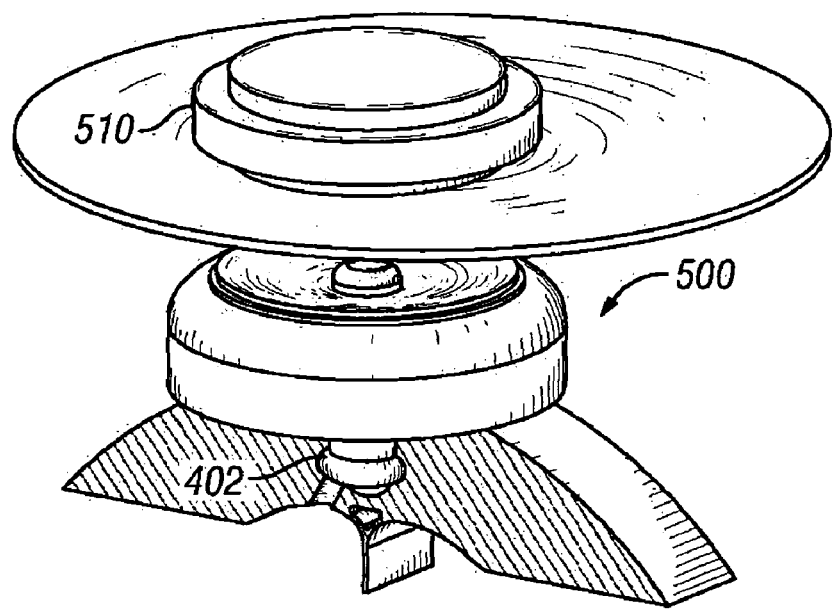
FIG. 5B depicts an electromagnetic device positioned adjacent to the ear drum of the patient for driving the diaphragm device of FIG. 5A.

In other embodiments, active driving mechanisms can be utilized to create movement of the cochlear fluid. FIG. 5A depicts diaphragm device 500 in which ferrous magnetic material 501 is attached to the diaphragm. An external magnetic field can then be generated to actuate movement of the magnetic material 501 thereby creating movement of the diaphragm and causing movement of the cochlear fluid. FIG. 5B depicts electromagnetic device 510 positioned adjacent to the ear drum of the patient. Electromagnetic device 510 can be implemented using conventional techniques (e.g., multiple windings of conductive material, optionally, about a magnetic core). Known hearing devices utilize magnetic fields to drive an interior to the ear canal and such external devices can be adapted according to some embodiments. Accordingly, the audio processing and magnetic field driving functionality shall not be discussed at length herein. It shall be appreciated, although such known external sound processing and magnetic field generating devices can be employed, the internal magnetic drivable diaphragm device of some embodiments is unique in its manner of adaptation for access to the cochlear fluid. In another embodiment, the driving coil could be integrated with diaphragm device 500 and a suitable electrical lead provided to connect with a sound processing module. In yet another embodiment, the electrical lead from the sound processing module (e.g., a device similar to conventional hearing aid "behind-the-ear" components) could be electrically coupled to a piezo or other transducing element that is mechanically coupled to the diaphragm.

Figure 5C:
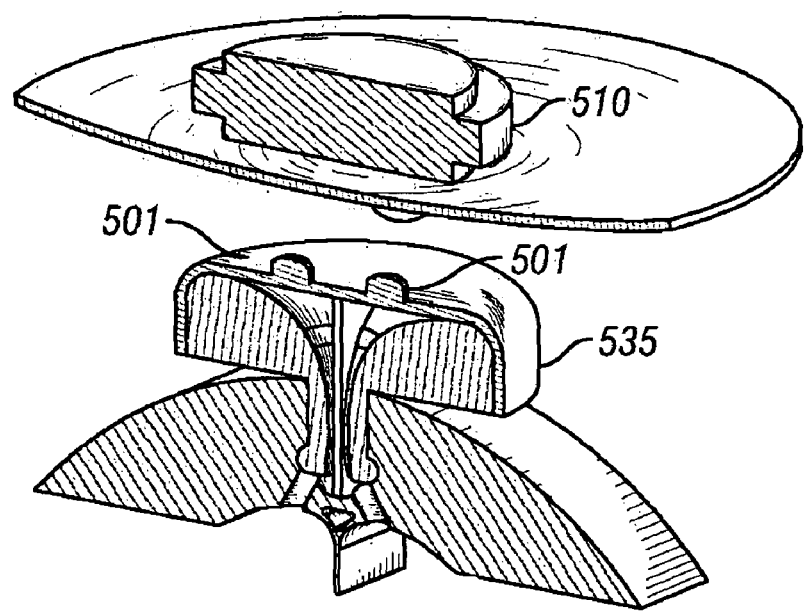
FIG. 5C depicts a cross-sectional view of a magnetic diaphragm device according to another embodiment.

FIG. 5C depicts a cross-sectional view of magnetic diaphragm device 535 according to another embodiment. Device 535 is a dual chamber device similar to device 425. Device 535 further includes two portions of magnetic material 501 which are disposed in opposite orientations (i.e. their north and south poles are disposed opposite to each other). Again, this design enables positive pressure to be created in one scala with simultaneously negative pressure in the other scala.

Figure 6A:
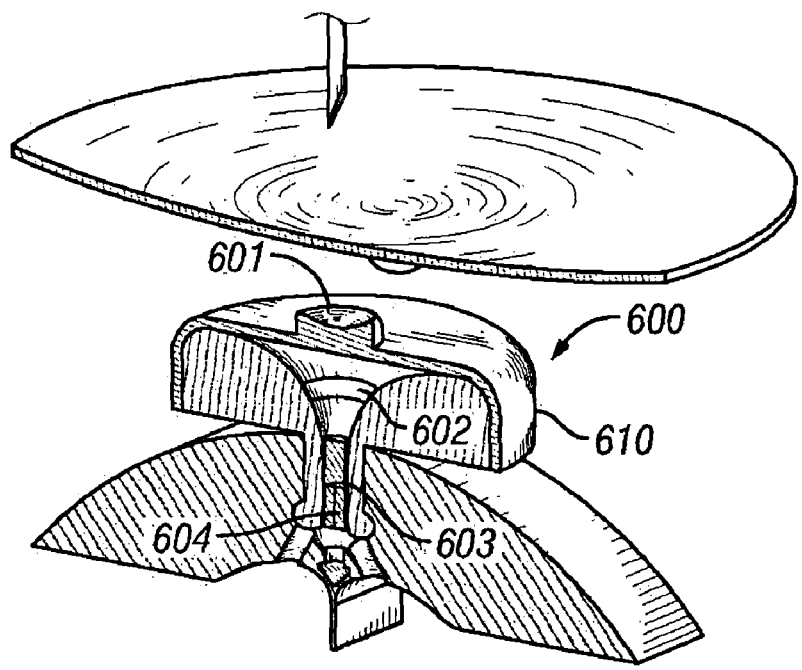
FIGS. 6A-6B depict a diaphragm device including a reservoir for storing a pharmaceutical agent according to another representative embodiment.
Figure 6B:
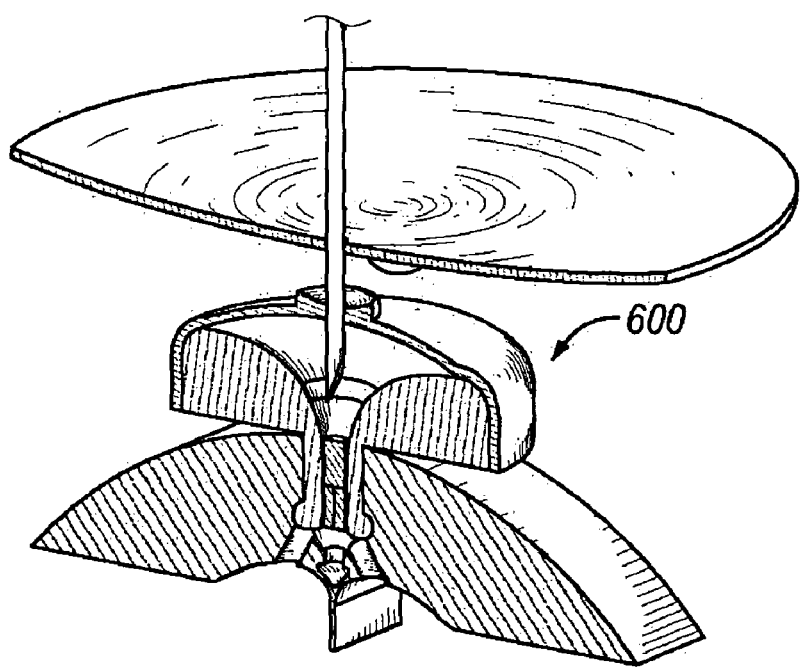

FIG. 6A depicts diaphragm device 600 according to another representative embodiment. Device 600 further includes drug pump functionality. A suitable pharmaceutical agent is introduced using a needle which is inserted through the patient's ear drum and through septum 601 of device 600. The pharmaceutical agent is stored in reservoir 602. Diaphragm 610 is fabricated using an elastic material adapted to expand upon introduction of the pharmaceutical agent as shown in FIG. 6B. The energy stored in the expansion of the elastic material 610 is used to drive the pharmaceutical agent through filter 603 and flow restrictor 604. The flow rate is largely determined by the elasticity of the deformable material 610 and the characteristics of the flow restrictor.

Figure 7A:
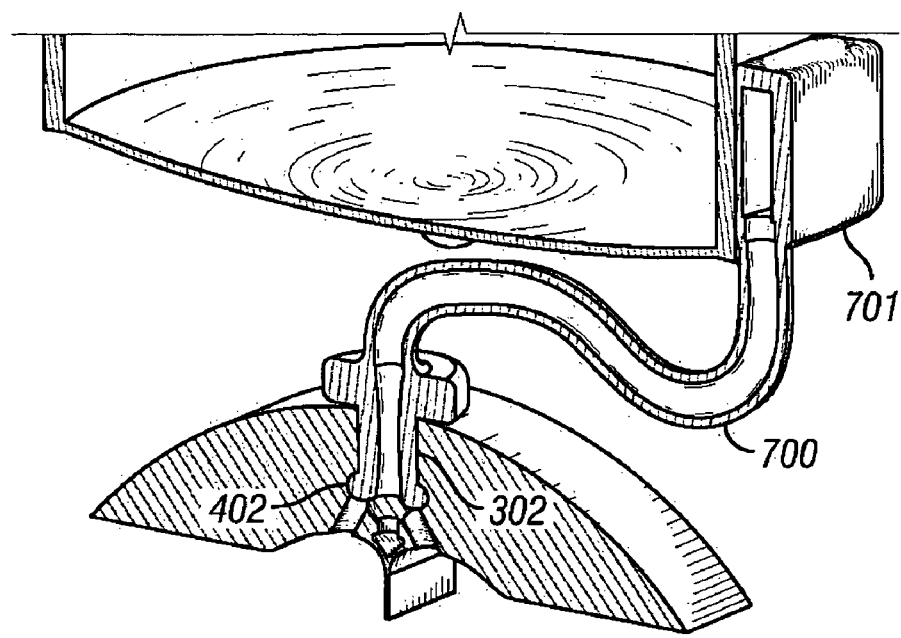
FIG. 7A depicts a catheter adapted to be fluidically coupled to the scala tympani and/or the scala vestibuli via a hole according to one representative embodiment.

In another embodiment, hearing device may comprise fluidic microphone amplification to drive movement in the cochlear fluid to treat the hearing loss of the patient. As shown in FIG. 7A, catheter 700 may be adapted to be fluidically coupled to the scala tympani and/or the scala vestibuli via hole 302. Deformable portion 402 is provided at the distal end of catheter 700 for coupling within cavity 315. Fluid within catheter 700 can be driven and, thereby, the fluid within the respective scala(s) can be driven. In the embodiment shown in FIG. 7A, the fluid within catheter 700 is driven by diaphragm device 701 placed in the ear canal, just under the skin.

Figure 7B:
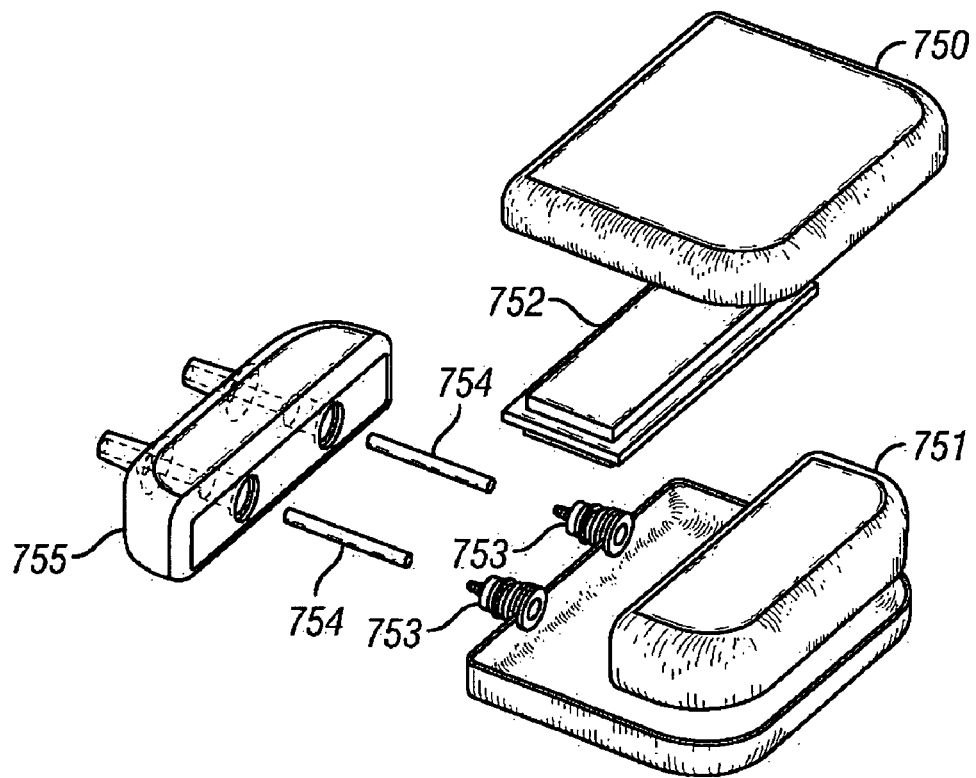
FIG. 7B depicts a fluid-driving sound processor system for use with the catheter of FIG. 7A according to one representative embodiment.

In another embodiment, the fluid in catheter 700 can be actively driven. FIG. 7B depicts fluid-driving sound processor system 750 for use with catheter 700 according to one representative embodiment. Sound processor system 750 may be implemented within a hermetically sealed titanium can in one embodiment, although any suitable packaging may be applied. Sound processor system 750 may include one or more microphones (not shown) to sample acoustical signals. The microphone(s) can be integrated on the exterior of the case of system 700 or provided separately. System 750 comprises battery 751 for powering system 750. System 750 further comprises electronics 752 for controlling the operations of system 750. In one embodiment, electronics 752 comprises a microcontroller with suitable audio processing algorithms stored in the embedded memory of the microcontroller or in other memory of system 750. Any suitable known audio processing algorithms (such as those commonly employed within hearing aids) may be utilized. The processing algorithms process digital samples of the audio signals obtained using the microphone(s).

The processed signals are then utilized to drive one or more sound ports 753 (e.g., audio transducers, piezo devices, etc.). Each sound port creates vibrations in the fluid within a respective fluid tube 754. Fluid tube 754 is adapted to be placed in fluid communication with a respective catheter 700 via header 755. Electronics 752 control sound port 753 to provide an appropriate amount of signal gain to address the hearing loss of the patient thereby driving the cochlear fluid by an amount appropriate to treat the patient's hearing loss. When two sound ports 753 and catheters 700 are employed, one catheter 700 may be used to drive fluid within the scala tympani and the other catheter 700 can be used to drive fluid within the scala vestibuli in one embodiment.

Figure 8A:
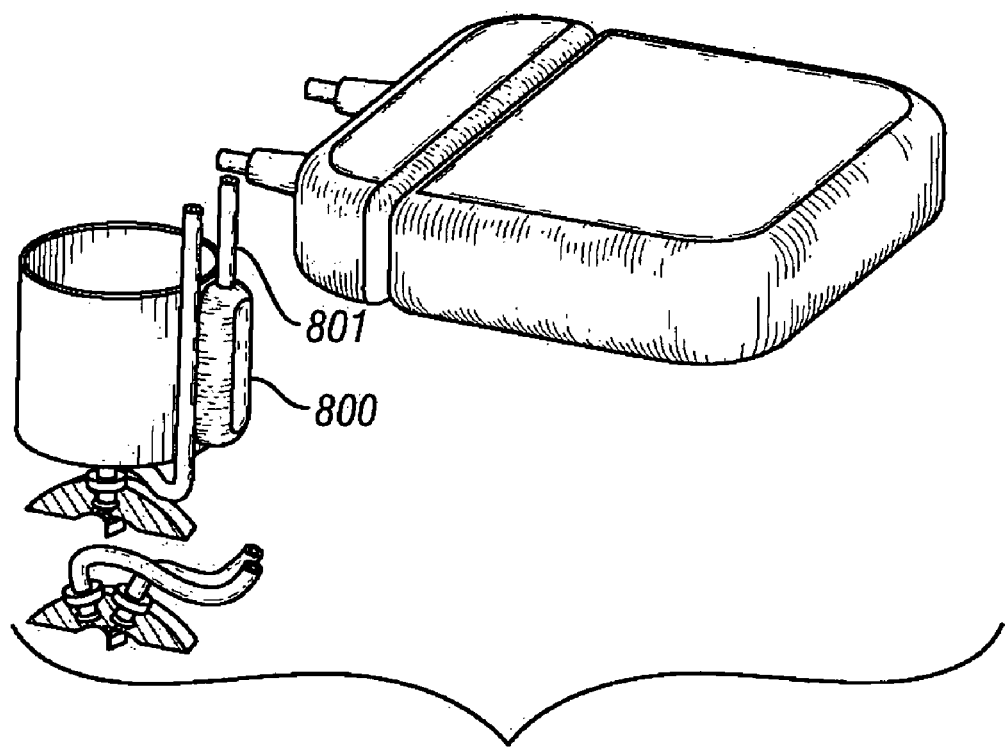
FIG. 8A depicts a fluidic microphone which generates movement within the fluid in a catheter according to one representative embodiment.
Figure 8B:
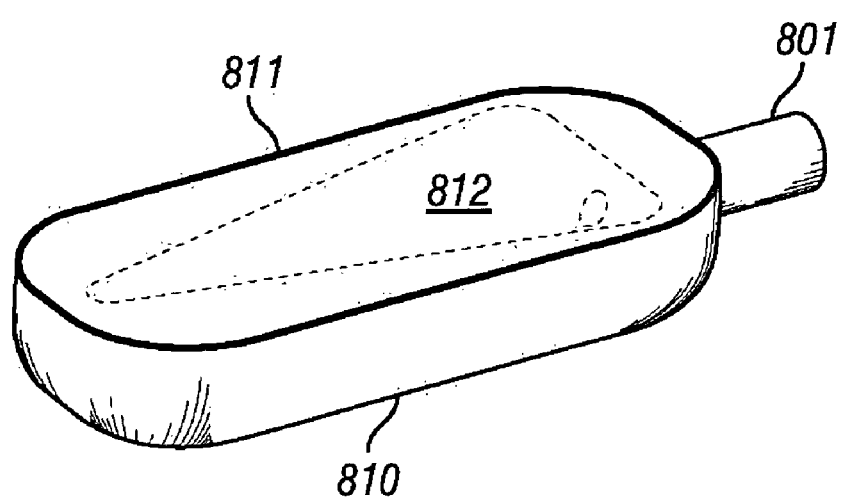
FIG. 8B depicts a pneumatic microphone for converting audio signals into movement in the fluid of the catheter of FIG. 8A according to one representative embodiment.

In another embodiment, one of the sound ports 753 can be utilized to receive audio signals. FIG. 8A depicts fluidic microphone 800 which generates movement within the fluid in catheter 801. The movement within the fluid in catheter 801 can be detected and converted into digital samples for processing by the electronics 752 of system 750. FIG. 8B depicts pneumatic microphone 810 for converting audio signals into movement in the fluid of catheter 801. Pneumatic microphone 810 comprises reservoir 812 and flexible diaphragm element 811. Vibrations contacting diaphragm 811 cause diaphragm 811 to vibrate thereby causing movement within the fluid in reservoir 812. The positive or negative pressure within reservoir is fluidically communicated to the fluid within catheter 801.

Figure 8C:
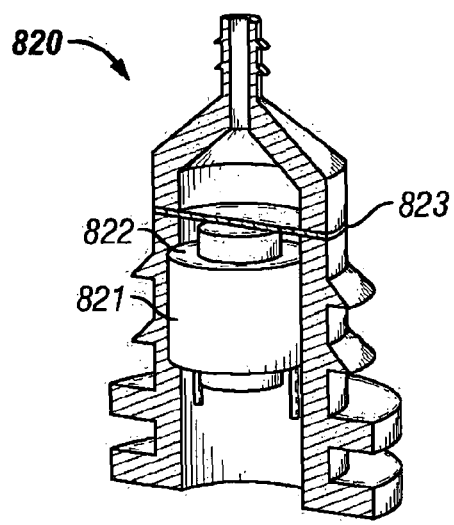
FIG. 8C depicts an electromagnetic device for detecting movement in the fluid of the catheter of FIG. 8A according to one representative embodiment.
Figure 8D:
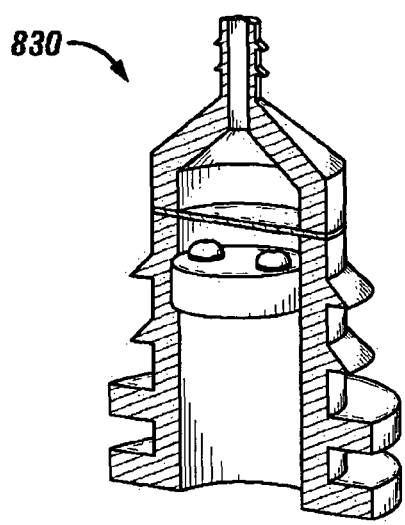

FIG. 8C depicts electromagnetic device 820 for detecting movement in the fluid of catheter 801. Device 820 comprises diaphragm 823. Movement in fluid contacting diaphragm 823 causes movement in magnetic 822. The movement in magnet 822 includes a change in current flow in coil 821 which can be sampled using conventional electronic circuitry. In an alternative embodiment, optic reflection may be employed to detect movement in diaphragm 823 as shown in device 830 of FIG. 8D.

Figure 9A:
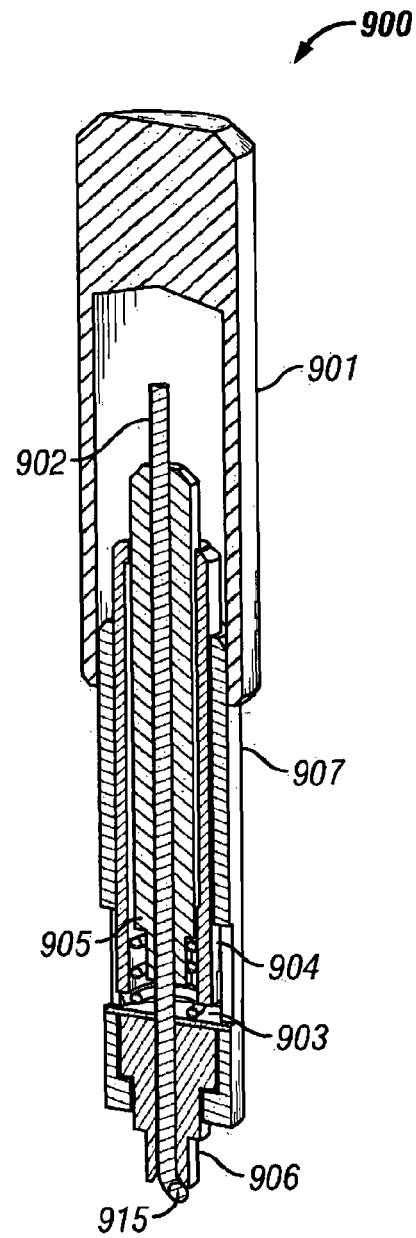
FIG. 9A depicts a drill bit for creating a side cavity within osseous tissue adjacent to the promontory of a patient according to one representative embodiment.

FIG. 9A depicts drill bit 900 for creating a side cavity within osseous tissue adjacent to the promontory of a patient according to one representative embodiment. Drill bit 900 comprises shaft 901 that is preferably adapted to fit on the end of conventional medical drills which are commercially available. Drill bit 900 comprises shape-memory wire 902 (e.g., fabricated using Nitinol according to one preferred embodiment.). Shape-memory wire 902 comprises tip end 915 which is adapted to extend in a generally perpendicular or in an otherwise generally lateral manner from the central axis of drill bit 900 under certain conditions as will be discussed below. Diamond grit is preferred applied to tip end 915 to permit tip end 915 to remove osseous tissue during operation of the drill.

Wire 902 is welded to curve loading sleeve 905 which in turn is welded to extension adjustment sleeve 904. Wire 902, curve loading sleeve 905, extension adjustment sleeve 904, are contained within outer sleeve 907 and are moveable relative to outer sleeve 907. Spring 903 is provided to bias these components relative to outer sleeve 907 and insertion sleeve 906. In a relaxed position, spring 903 causes wire 902 to be substantially held within outer sleeve 907. When suitable force is applied, curve loading sleeve 905 contacts and compresses spring 903. At the same time, wire 903 is pushed beyond the distal end of insertion sleeve 906. The shape memory of wire 903 causes tip end 915 to extend in a generally lateral direction.

Figure 9B:
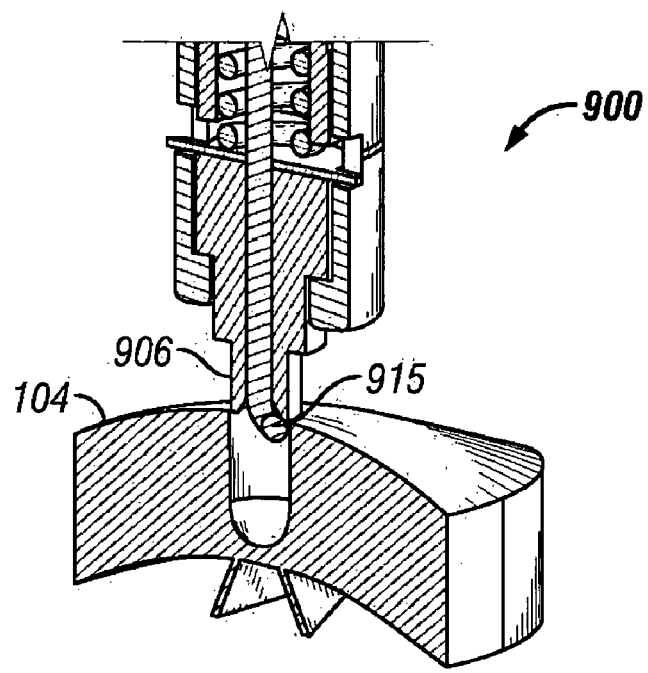
FIGS. 9B-9F depict the drill bit of FIG. 9A during creation of a side cavity within osseous tissue of a patient according to one embodiment.
Figure 9C:
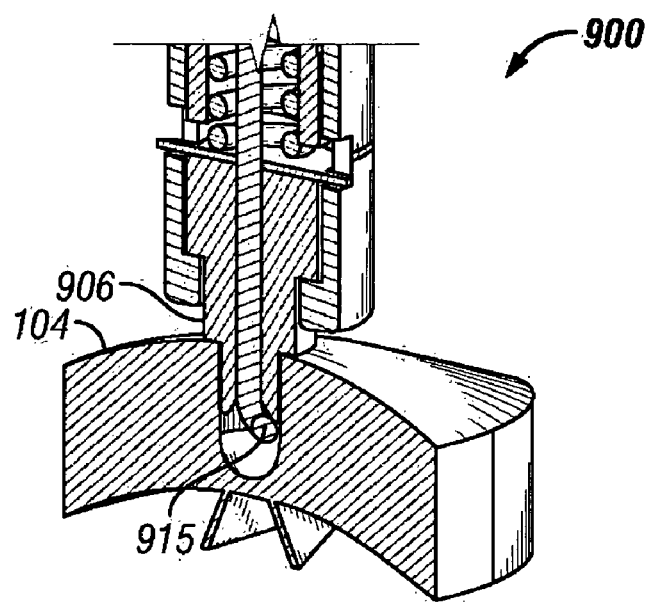
Figure 9D:
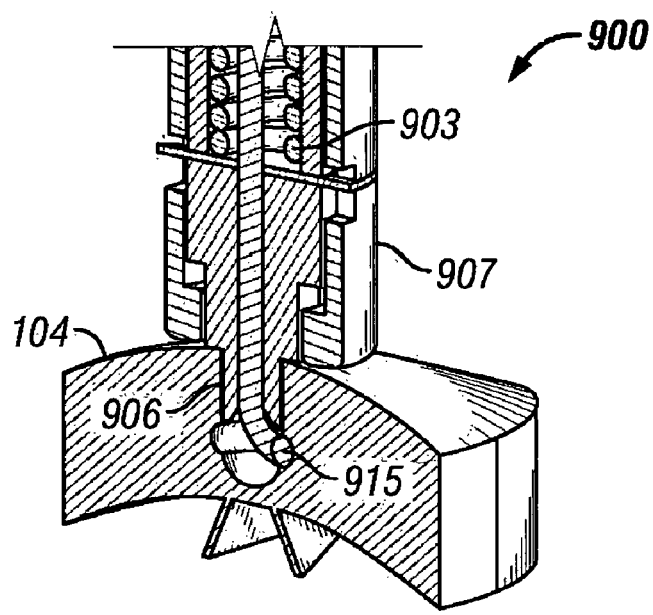
Figure 9E:
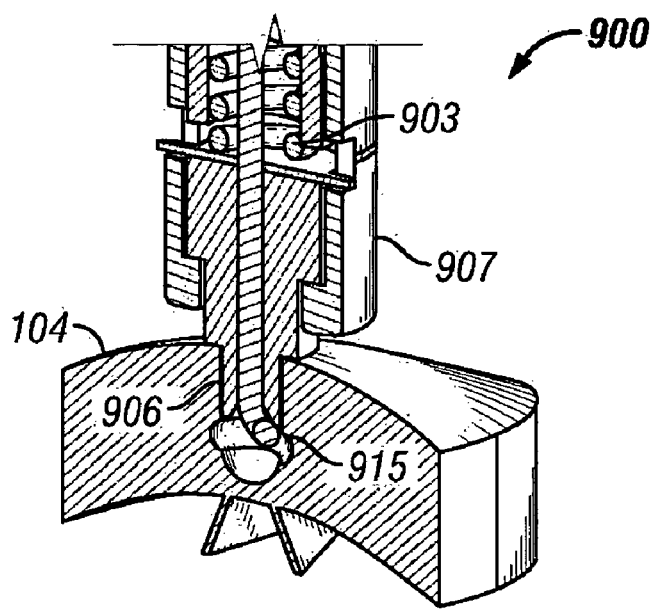
Figure 9F:
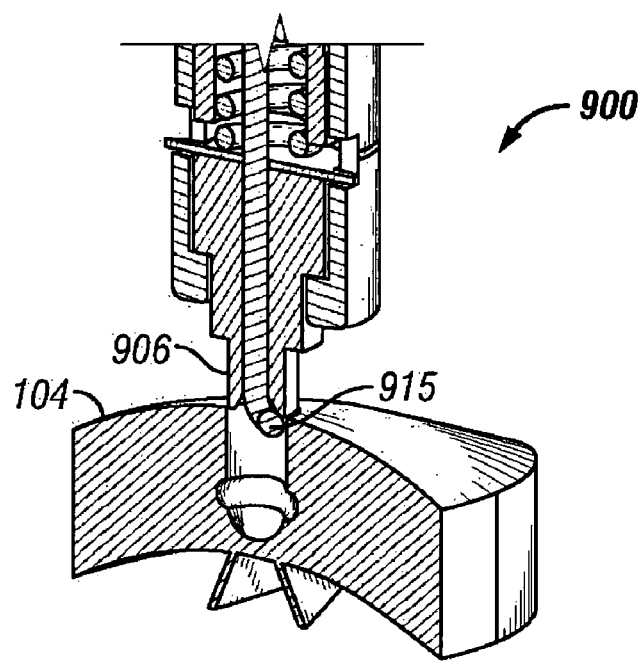

FIGS. 9B-9F depict drill bit 900 during creation of a side cavity within osseous tissue of a patient according to one embodiment. FIG. 9B depicts drill bit 900 being brought into proximity of a previously created hole in osseous tissue in the promontory 104 of a patient. As shown in FIG. 9B, the various components of drill bit 900 are disposed in a stable state in which tip end 915 is largely confined by insertion sleeve 906 (e.g., tip end 915 does not substantially extend beyond the outer diameter of insertion sleeve 906). As shown in FIG. 9C, the physician places drill bit 900 such that insertion sleeve 906 is inserted into the previously created hole. Force is then applied to drill bit 900 causing outer sleeve 907 to contact the promontory as shown in FIG. 9D. The force compresses spring 903. Also, the force causes relative movement of outer sleeve 907 relative to insertion sleeve 906 and, hence, wire 902 moves relative to insertion sleeve 906. During operation of the drill, the shape memory of the material of wire 902 causes tip end 915 of wire 902 to extend laterally relative to the central axis of drill bit 900 as osseous tissue is removed by tip end 915. Thereby, the side cavity is created. After the side cavity is created, the force pressing outer sleeve 907 against the promontory is removed and spring 903 causes tip end 915 to return to its previous position relative to insertion sleeve 906 as shown in FIG. 9E. Drill bit 900 is then removed as shown in FIG. 9F.

Figure 10A:
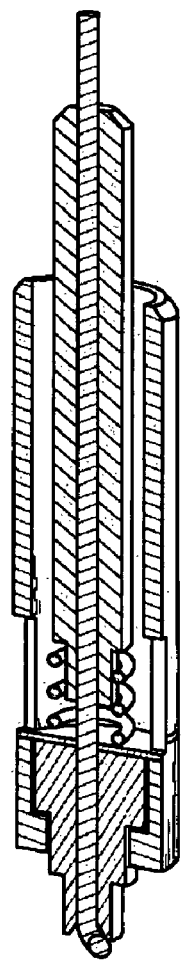
FIGS. 10A-10E depicts various stages of assembling a drill bit according to one representative embodiment.
Figure 10B:
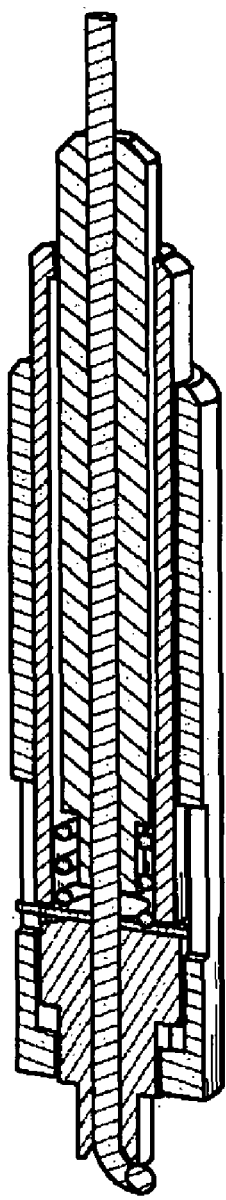
Figure 10C:
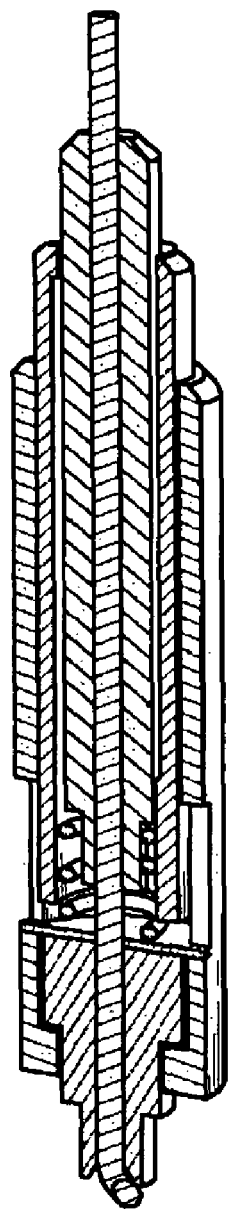
Figure 10D:
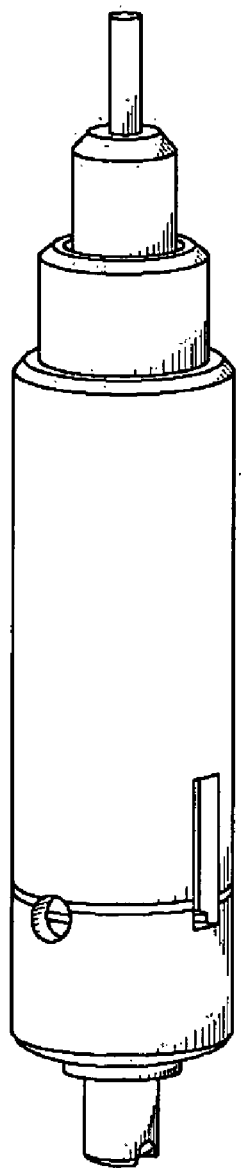
Figure 10E:
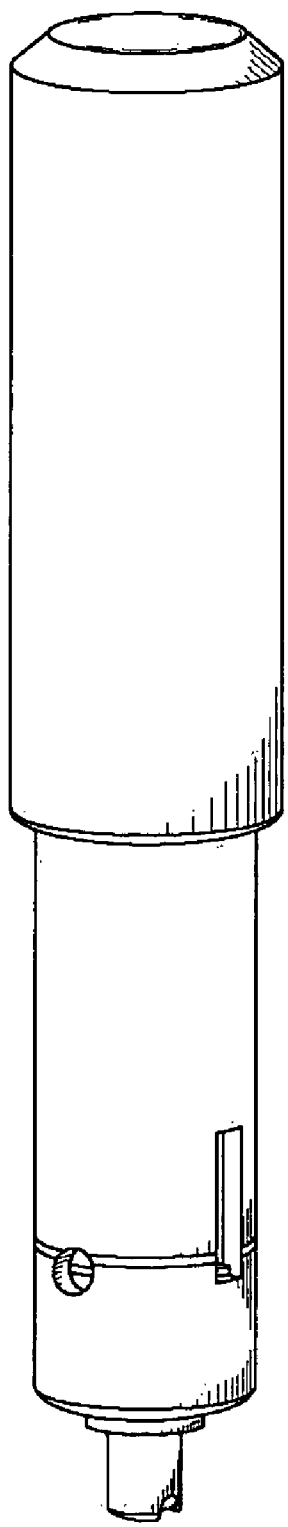

FIG. 10A depicts a stage of assembling drill bit 900 according to one representative embodiment. As shown in FIG. 10A, wire 902 and curve loading sleeve 905 are pulled in opposite directions thereby compressing spring 903 and the tip end 915 of wire 902 to retract into insertion sleeve 906. Curve loading sleeve 905 is then laser welded, crimped, or swaged to wire 902. A second stage is shown in FIG. 10B. Curve loading sleeve 905 and wire 902 are pushed forward until wire 902 is extended by the desired amount (e.g., by the amount necessary for the side cavity). Extension adjustment sleeve 904 is then laser welded, crimped, or swaged to curve loading sleeve 905 as it is being pressed against the activation indicator as shown in FIG. 10B. Outer sleeve 907 is then pressed against the shoulder of insertion sleeve 906 and is laser welded, crimped, or swaged to insertion sleeve 906 as shown in FIG. 10C. In FIG. 10D, the activation indicator is laser spot welded to insertion sleeve 906. In FIG. 10E, drill shaft 901 is laser welded, crimped, or swaged to outer sleeve 907.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure that processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A device for treating hearing loss by facilitating stimulation of cochlear fluid through the promontory bone, comprising:
   a diaphragm;
   a body portion coupled to the diaphragm, the body portion and diaphragm defining at least a portion of a reservoir;
   a neck portion extending away from the body portion, the neck portion comprising an outer diameter; and
   a deformable member disposed on the neck portion, wherein at least a portion of the deformable member is configured to extending beyond the outer diameter of the neck portion when the deformable member is not compressed;
   wherein the neck portion is adapted to be inserted into a channel formed in the promontory bone of the patient, the neck portion being further adapted to permit cochlear fluid to flow through the neck portion and into the reservoir;
   wherein the deformable member is adapted to engage a cavity formed in the channel and hold the neck portion in the channel.

2. The device of claim 1 further comprising: a magnetic drive mechanism for driving the diaphragm.

3. The device of claim 2 wherein the magnetic drive mechanism comprises ferrous magnetic material coupled to the diaphragm.

4. The device of claim 2 wherein the magnetic drive mechanism comprises a magnetic coil that is coupled to an electrical lead.

5. The device of claim 1 further comprising: a piezo-drive element for driving the diaphragm.

6. The device of claim 1 wherein the body portion comprises a second reservoir and the neck portion permits cochlear fluid to flow into both reservoirs through separate fluid paths.

7. The device of claim 1 wherein the diaphragm is configured to vibrate at a limited subset frequency range of acoustical frequencies audible to humans.

8. The device of claim 1 further comprising: a piston that is mechanically coupled to the diaphragm, the piston extending into the neck portion.

* * * * *